(12) United States Patent
Calasso et al.

(10) Patent No.: US 7,819,822 B2
(45) Date of Patent: Oct. 26, 2010

(54) BODY FLUID SAMPLING DEVICE

(75) Inventors: Irio Guiseppe Calasso, Arth (CH); Patrick Griss, Zürich (CH); Emad Sarofim, Hagendorn (CH); Rainer Jaeggi, Wohlen (CH); Uwe Kraemer, Ilvesheim (DE); Dave Hasker, San Jose, CA (US); Volker Zimmer, Laumersheim (DE); Wilfried Schmid, Mannheim (DE); Otto Fuerst, Viernheim (DE); Hans List, Hessenneck-Kailbach (DE); Hans-Peter Haar, Wiesloch (DE); Theo Arnitz, Waghaeusel (DE); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 180 days.

(21) Appl. No.: 11/470,368

(22) Filed: Sep. 6, 2006

(65) Prior Publication Data

US 2007/0016103 A1    Jan. 18, 2007

Related U.S. Application Data

(63) Continuation of application No. PCT/EP2005/002357, filed on Mar. 7, 2005.

(60) Provisional application No. 60/642,956, filed on Jan. 11, 2005.

(30) Foreign Application Priority Data

Mar. 6, 2004   (EP)   .................... 04005385

(51) Int. Cl.
A61B 5/00     (2006.01)

(52) U.S. Cl. ....................... 600/583; 600/584

(58) Field of Classification Search ............... 600/573, 600/583; 606/181, 183
See application file for complete search history.

(56) References Cited

U.S. PATENT DOCUMENTS 4,218,421 A    8/1980    Mack, Jr. et al.

(Continued)

FOREIGN PATENT DOCUMENTS

CN    1407327 A    4/2003

(Continued)

OTHER PUBLICATIONS

Office Action received in counterpart U.S. Appl. No. 11/470,021 mailed Feb. 27, 2009.

(Continued)

*Primary Examiner*—Max Hindenburg
*Assistant Examiner*—Michael C Stout
(74) *Attorney, Agent, or Firm*—Woodard Emhardt Moriarty McNett & Henry LLP

(57) ABSTRACT

Body fluid sampling device comprising a skin-piercing element having a collection zone for receiving body fluid, and the device further comprising a fluid receiving means remote spaced apart from the collection zone so that body fluid in the collection zone will not contact the fluid receiving means initially. The collection zone takes up a very small volume of body fluid of about 10 to 500 nl in a very short time period of less than 0.5 seconds. The fluid receiving means may have a test zone for performing an analytical reaction. Fluid sample from the collection zone is automatically or manually transported to the fluid receiving means to contact the fluid with the test zone.

45 Claims, 9 Drawing Sheets

U.S. PATENT DOCUMENTS

| | | | |
|---|---|---|---|
| 5,163,442 A | 11/1992 | Ono | |
| 5,318,584 A | 6/1994 | Lange et al. | |
| 5,582,184 A * | 12/1996 | Erickson et al. | 600/576 |
| 5,762,770 A | 6/1998 | Pritchard et al. | |
| 5,801,057 A | 9/1998 | Smart et al. | |
| RE36,268 E | 8/1999 | Szuminsky et al. | |
| 6,063,040 A | 5/2000 | Owen et al. | |
| 6,132,449 A | 10/2000 | Lum et al. | |
| 6,364,890 B1 | 4/2002 | Lum et al. | |
| 6,375,626 B1 | 4/2002 | Allen et al. | |
| 6,589,260 B1 | 7/2003 | Schmelzeisen-Redeker et al. | |
| 6,612,111 B1 | 9/2003 | Hodges et al. | |
| 6,660,018 B2 * | 12/2003 | Lum et al. | 606/181 |
| 6,821,483 B2 * | 11/2004 | Phillips et al. | 422/58 |
| 6,988,996 B2 | 1/2006 | Roe et al. | |
| 7,005,857 B2 | 2/2006 | Stiene et al. | |
| 2002/0043463 A1 | 4/2002 | Shenderov | |
| 2002/0114715 A1 | 8/2002 | Yoon et al. | |
| 2002/0168290 A1 | 11/2002 | Yuzhakov et al. | |
| 2003/0018282 A1 | 1/2003 | Effenhauser et al. | |
| 2003/0028125 A1 * | 2/2003 | Yuzhakov et al. | 600/583 |
| 2003/0059350 A1 * | 3/2003 | Sacherer | 422/104 |
| 2003/0073931 A1 | 4/2003 | Boecker et al. | |
| 2003/0083685 A1 | 5/2003 | Freeman et al. | |
| 2003/0205632 A1 | 11/2003 | Kim et al. | |
| 2003/0212344 A1 | 11/2003 | Yuzhakov et al. | |
| 2004/0022681 A1 | 2/2004 | Hantschel et al. | |
| 2004/0064068 A1 * | 4/2004 | DeNuzzio et al. | 600/583 |
| 2004/0176732 A1 | 9/2004 | Frazier et al. | |
| 2004/0193072 A1 | 9/2004 | Allen | |
| 2005/0043597 A1 | 2/2005 | Xie | |
| 2005/0149088 A1 * | 7/2005 | Fukuda et al. | 606/181 |
| 2005/0234368 A1 | 10/2005 | Wong et al. | |
| 2006/0087064 A1 | 4/2006 | Daniel et al. | |
| 2006/0100654 A1 * | 5/2006 | Fukuda et al. | 606/181 |
| 2006/0276724 A1 * | 12/2006 | Freeman et al. | 600/583 |
| 2007/0016103 A1 | 1/2007 | Calasso et al. | |
| 2007/0038149 A1 | 2/2007 | Calasso et al. | |
| 2007/0126536 A1 | 6/2007 | Fork et al. | |
| 2007/0250099 A1 * | 10/2007 | Flora et al. | 606/181 |
| 2008/0268669 A1 | 10/2008 | Van Schuylenbergh et al. | |

FOREIGN PATENT DOCUMENTS

| | | |
|---|---|---|
| CN | 1431884 A | 7/2003 |
| EP | 0199484 B1 | 10/1986 |
| EP | 0 458 405 | 11/1991 |
| EP | 0299517 B1 | 6/1993 |
| EP | 0565970 B1 | 6/1994 |
| EP | 0723418 B1 | 7/1996 |
| EP | 1101443 A2 | 5/2001 |
| EP | 1 360 933 | 11/2003 |
| EP | 1360931 A1 | 11/2003 |
| EP | 1 371 419 A1 | 12/2003 |
| EP | 1424040 A1 | 6/2004 |
| EP | 1 508 304 | 10/2006 |
| EP | 1 360 934 | 12/2006 |
| GB | 1 418 337 | 12/1975 |
| WO | WO 97/18036 | 5/1997 |
| WO | WO97/42888 A1 | 11/1997 |
| WO | WO01/66010 A1 | 9/2001 |
| WO | WO 01/72220 A1 | 10/2001 |
| WO | WO01/72220 A1 | 10/2001 |
| WO | WO 02/07503 | 1/2002 |
| WO | WO 02/49507 | 6/2002 |
| WO | WO02/50534 A1 | 6/2002 |
| WO | WO02/0622210 A1 | 8/2002 |
| WO | WO 02/100253 | 12/2002 |
| WO | WO 01/72220 A1 | 7/2003 |
| WO | WO2005/084530 A2 | 9/2005 |
| WO | WO2005/084545 A1 | 9/2005 |
| WO | WO2005/084546 A3 | 9/2005 |

OTHER PUBLICATIONS

Non-Final Office Action received in related U.S. Appl. No. 11/469,123, mailed Jun. 2, 2009.
U.S. Appl. No. 11/470,021 Final Office Action mailed Sep. 8, 2009.
Non-Final Office Action received in related U.S. Appl. No. 11/469,123, mailed Dec. 10, 2009.
English translation-in-part of Japanese Unexamined Patent Publication No. 150458/1991.
Non-Final Office Action received in related U.S. Appl. No. 11/469,123, mailed Dec. 10, 2009.

* cited by examiner

BODY FLUID SAMPLING DEVICE

REFERENCE TO RELATED APPLICATIONS

This application is a continuation of International Application No. PCT/EP2005/002357 filed Mar. 7, 2005, which claims the benefit of U.S. Provisional Application No. 60/642,956, filed Jan. 11, 2005, which are incorporated by reference in their entirety.

BACKGROUND

The present invention relates to the field of body fluid analysis in order to monitor the concentration of analytes such as blood glucose concentration.

The invention concerns a device and system for sampling small amounts of body fluid. A body fluid sampling device comprises a skin-piercing element with a collection zone (e.g. a fluid pathway) for receiving body fluid therein. At least a portion of the collection zone is open to the environment so that fluid can be sampled. The sampling device or a separate element comprises a fluid receiving means which is out of fluidic contact with the collection zone of the skin-piercing element so that sampled fluid in the collection zone will not contact the fluid receiving means initially. The body fluid sampling device with connected collection zone or a system comprising a body fluid sampling device and fluid receiving means can be brought into a second state in which at least a portion of the collection zone contacts the fluid receiving means so that fluid is transferred. Based on signals from a test zone of the fluid receiving means analyte concentration can be determined.

Systems for sampling body fluids are already known in the prior art in which body fluid is taken up into a disposable element. Blood collection and analytical systems are known from document EP 0 199 484 for example which comprises a disposable unit with a capillary to collect body fluid and to transport the body fluid into a detection area. The further development of this concept is described in WO 97/42888. The arrangement described in this document is particularly suitable for collecting relatively small amounts of body fluids which is primarily accomplished by pressing a ring onto the area surrounding a collection site and applying a pump movement. A system for analysis based on small amounts of interstitial fluid is known from EP 0 723 418. For this purpose a very thin hollow needle is inserted into the dermis and interstitial fluid is conveyed through the needle to a test zone by applying pressure to the area surrounding the puncture site. A highly miniaturized arrangement which also utilizes a hollow needle to withdraw body fluid is known from U.S. Pat. No. 5,801,057. A particular advantage of this arrangement is the extremely thin needle which can be inserted into the arm region of a patient essentially without any pain.

Whereas the arrangement described in U.S. Pat. No. 5,801,057 already fulfils numerous practical requirements, some features are in need of improvement. A general problem with the sampling devices according to the previously mentioned document is to manufacture the hollow needle cost-effectively and as small as possible.

With this aim body fluid samplers which have an open collection zone have been contemplated. US 2003/0018282 and US 2003/0028125 both describe skin-piercing devices which have an open channel for body fluid sampling which at least partially is located in a region of a piercing needle. Body fluid sampled into the collection zone is transferred to a testing zone which is fixed to the skin-piercing element. In particular US 2003/0028125 describes that the skin-piercing element is integral with a part of a test strip. A further document that contemplates a similar sampling and testing device providing a pooling area is described in US 2002/0168290.

WO 01/72220 describes a fluid sampling and analysis device with a dermal penetration probe. Said penetration probe being in direct fluid communication with an analysis chamber. Accordingly this device design has the disadvantage that sterilization of the penetration probe which is regularly achieved by gamma radiation destroys the test chemistry located in the analysis chamber. Further sampling and analysis are spatially fixed to one another and therefore need to be close together to allow efficient sample transfer.

SUMMARY

The prior art sampling and testing devices describe embodiments where sample from a capillary channel is directly transferred to a testing zone which is in fluidic contact with the channel. Contrary to that the present invention proposes body fluid sampling and testing devices where the collection zone in a phase in which sample is taken up is out of fluidic contact with a testing zone. In a second phase, after having taken up a fluid sample into the collection zone, at least a portion of the collection zone is being transferred in a second position in which at least a portion of the collection zone comes into contact with a fluid receiving means that receives fluid from the collection zone. Alternatively the fluid receiving means can be moved or both, the fluid receiving means as well as the collection zone may be moved.

In a first preferred embodiment a body fluid sampling device comprises a skin-piercing element having a collection zone for receiving body fluid and a fluid receiving means comprising a test zone. Said fluid receiving means being out of fluidic contact with said collection zone so that fluid present in said collection zone will not contact the fluid receiving means. Alternatively the fluid receiving means may not have an integrated test zone but it is contacted with a separate test zone to achieve analytical testing.

A second preferred embodiment comprises an integrated device with a skin-piercing means having a fluid collection zone as well as a fluid receiving means with a test zone. Said integrated device being adapted to undergo a physical change (in particular a movement of the collection zone relative to the fluid receiving means) upon actuation so as to assume a contacting state in which a fluid in said collection zone contacts said fluid receiving means.

A third preferred embodiment concerns a device according to the first preferred embodiment, wherein said device has a moveable portion which can be moved and at least a portion of said fluid collection zone or of said fluid receiving means is located on said moveable portion.

A fourth preferred embodiment concerns a device according to the first preferred embodiment, wherein body fluid received in said collection zone is moved by electrical actuation onto the fluid receiving means.

A fifth preferred embodiment comprises a device according to the first preferred embodiment, wherein body fluid received in said collection zone is transferred into contact with the fluid receiving means without using body fluid as transport means.

According to a sixth preferred embodiment of the invention the body fluid sampling device is contacted with a separate transport element to receive fluid which then in turn is contacted with a test zone on a separate element.

The present invention in particular is useful for handheld testing systems.

Further it is preferred if the skin-piercing element is a disposable that is only used once. It is also preferred to employ disposable fluid receiving means which are only used once.

According to an embodiment of the prior art the transport means comprises e. g. a capillary reaching from the collection zone to the fluid receiving means (e.g. EP 1 360 931). The body fluid is taken up at the test zone and is transferred to contact the fluid receiving means by capillary actuation, i. e. the subsequently picked up body fluid pushes the sample to the fluid receiving means. This additionally needed fluid volume, the so-called dead volume, serves as transport means to transfer the fluid used for the analysis to contact the fluid receiving means. This means that by principle more body fluid volume has to be collected than is needed for the measurement and this dead volume increases with increasing transfer distance. According to the present invention contrary to the prior art there is no dead volume needed. Ideally the whole sample volume that is collected in the collection zone is transferred to the fluid receiving means to be used for the measurement. Of course, it is likely that some sample remains in the collection zone, as it is the case by using a capillary. Furthermore, according to the present invention the body fluid volume needed to be sampled for measurement does not necessarily increase with increasing distance between collection zone and fluid receiving means.

Another advantage of the invention is, that due to the fact that skin-piercing element and fluid receiving means initially are not in fluidic contact, they can easily be separated in two parts. The skin-piercing element, or at least part of it, punctures the skin and therefore needs to be sterilized. Test zones, in the most cases however, are sensitive to sterilization. Seperating skin-piercing element and fluid receiving means into two parts solves this problem as the skin piercing element can be sterilized separately from the fluid receiving means an thus avoiding a destruction of the test chemistry.

The fluid receiving means may itself contain a test zone or it may be an element without a test zone that transports sample to a separate test zone. In both cases wetting of the test zone, however, can be initiated in a controlled manner by the contacting step. This triggering of test zone wetting has the advantage that the reaction time (i.e. the time between contacting a test chemistry with sample fluid and reading of test results) can be controlled which leads to higher accuracy of analyte determination.

A further advantage compared to the prior art sampling devices is that fluid sampling and contacting of the sampling device with a testing zone can be conducted at different locations. Fluid sampling for example can be done at the front end of a hand-held apparatus while contacting with a testing zone can be made within the apparatus. Due to this shuttle function of the skin-piercing element optics or other evaluation means can be moved into the interior of a housing which is advantageous with view to the limited space at the front end. Furthermore a physical separation of the test zone from blood during the sampling step avoids that test chemistry diffuses into the human body during sampling. The present invention therefore has significant advantages over the fluid sampling devices of the prior art.

One particular field of application of systems and devices for withdrawing small amounts of body fluid is the so-called spot monitoring in which the concentration of particular analytes present in body fluids is determined at a particular time. Such measurements can be carried out repeatedly at time intervals in order to monitor a change of analyte concentration. Such analysis employing disposable test elements has proven to be particularly advantageous especially in the field of blood sugar measurement by diabetics. If excessively high blood sugar values (hyperglycaemia) occur in a diabetic over a period of time, this can lead to serious long-term damage such as blindness and gangrene. If, on the other hand, a diabetic gets into a state of hypoglycaemia because he has for example injected too large a dose of insuline, this can become life-threatening if the diabetic falls into a so-called hypoglycaemic shock. A regular control of the blood sugar level enables the diabetic to avoid hyperglycaemic and hypoglycaemic states and also to learn how to coordinate his eating habits, bodily activity and insuline medication. In addition to improving and maintaining the health of diabetics, regular blood sugar monitoring also has considerable overall economic advantages since high costs for secondary diseases can be avoided. The reasons which prevent a more widespread and consequent use of blood sugar monitoring are primarily the pain caused by the required body fluid collection and the multiple handling steps of systems currently in the market. With the currently used systems the diabetic or medical staff must firstly obtain a drop of blood which is usually obtained from the finger pad. So-called lancing devices may be used to reduce pain. A lancing device must be firstly loaded with a lancet, tensioned, placed on the body surface and triggered. After the lancing process the user has to milk his finger in order to convey a drop of blood out of the puncture wound. Before this procedure the diabetic has to already place a test strip in a blood sugar measuring instrument and activate it. The drop of blood can now be applied to the test strip and after for example 10 s a blood sugar measurement is available. Finally the user has to dispose of the spent lancet and test strip. The present invention enables the process of blood sugar measurement to be greatly simplified.

The present invention, however, can be employed for other analytes as well. Further it is possible to analyse sampled fluid with different test zones simultaneously of subsequently.

Simplification of testing according to the present invention not only is advantageous for current users, it hopefully also has the effect that more people having diabetes or other diseases will test their blood glucose concentration or other parameters on a more regular basis.

A sampling device and system according to the present invention serves to withdraw small amounts of body fluid. Preferably, the body fluid sample is received in the collection zone while the collection zone is in the body, i. e. no blood needs to leak from the puncture site and the user does not need to milk his finger and to move the drop of blood on his finger to a test zone. Of course, it is also possible to use blood that leaks from the puncture site. In this context body fluids are understood in particular as blood, interstitial fluid and mixtures of these body fluids. Whereas conventional blood collection systems usually carried out sampling on the finger pad, the collection system according to the present invention can also be used to withdraw blood from alternative sites on the body such as the forearm and the palm.

A skin-piercing element for withdrawing small amounts of body fluid according to the present invention has a protruding portion with a sharpened end for piercing skin. Within at least a region of the protruding portion a collection zone is located which has the ability to collect body fluid. This in particular can be achieved by a capillary activity. At least a part of the body fluid receiving structure is open. A capillary structure is understood within the scope of the invention as a body which transports body fluid as a result of capillary forces. In case of a capillary channel fluid is transported towards the proximal end of the skin-piercing element when the distal area is contacted with body fluid. With regard to this embodiment the capillary structure according to the invention is similar to the open needle structures described in US 2003/0018282 and US 2003/0028125 to which reference is made herewith. However, an important difference is that these documents describe microneedles where the capillary channel is in fluidic contact with a test zone so that body fluid received in the capillary channel is directly applied to the test zone and hence initiates reaction.

Capillary structures in the collection zone may be manufactured by photolithographic methods like those described in the document U.S. Pat. No. 5,801,057 and which are known from the field of semiconductor technology. It is also possible to provide channels, grooves, holes etc. which are open to the outside in solid needles by milling, etching and such like. Such structures are preferably generated by etching processes as photochemical milling (PCM). PCM is based on optical pattern transfer and etch processes. It is known to be a micromachining technology.

In addition to the already mentioned methods for incorporating capillary structures into surfaces, it is also possible to generate the capillary channels by assembling bodies in a way that capillary gaps are created. Thus it is for example possible to fasten two or more solid needles together for example by welding such that the contact areas of the solid needles form capillary channels. In a corresponding manner it is also possible to twist wires or fibres together in the form of a stranded wire such that numerous contact areas are formed which generate the capillary channels. The wires or fibres might be made of metal, glass or carbon, and can be solid or hollow, for example it can be necessary to grind a lancet surface to achieve open capillaries. It is also possible that the capillary is not open to the environment for the whole time, e. g. it may be opened only during the skin-piercing step to collect the body fluid. Further skin-piercing elements with fluid pathways can be created by applying one or more layer of materials (e.g. laminated foils) onto a flat needle in a way that a capillary gap is created between the layers or is provided in one such layer.

The capillary structures according to the present invention are, however, not restricted to capillary channels leading from a distal to a proximal end of the skin-piercing element. Also porous structures or holes may be employed to sample fluid. With the present invention it is not essential that capillaries transport fluid over a macroscopic distance to achieve wetting of a test zone. Instead the collection zone and fluid receiving means are moved into proximity.

To achieve proper sampling of body fluid into the channel of the skin-piercing element and to enhance sampling speed it is preferred to employ hydrophilic materials, particularly for the collection zone. Alternatively or in addition to hydrophilic materials, hydrophilic coatings may be employed.

The skin-piercing devices are introduced into the skin and therefore have to be sterile to avoid infections and inflammations. According to this the skin-piercing elements may be packaged in a sterile way e. g. in a blister. In a preferred embodiment the tips of skin-piercing elements are covered by e. g. a plastic to avoid contamination after the skin-piercing elements are sterilized (e. g. by gamma-radiation). Particularly preferred are tip protections as described in WO 01/66010. Such tip protection covers which surround the needle can be produced easily and also can be removed easily so that an automatic removal within a system becomes feasible. A system for analysis according to the present invention may comprise an actuator to pull off a cap from the tip before skin-piercing is initiated. Alternatively the skin piercing element may be transferred into a position where the protective cap is held (e. g. by form-fit) and is removed from the skin-piercing element by moving the skin-piercing element away from the fixed cap. Preferably this movement can be conducted by a lancing drive or transport means which is employed anyhow. Even embodiments are possible where the protective cap is pierced by the lancing tip of the skin-piercing element as e. g. shown in FIG. 1 or 6 of WO 0166010.

Alternatively it is possible to sterilize the skin-piercing element within the handheld device directly before use by e. g. ultraviolet radiation or heat.

DESCRIPTION OF SELECTED EMBODIMENTS

Figure 1:
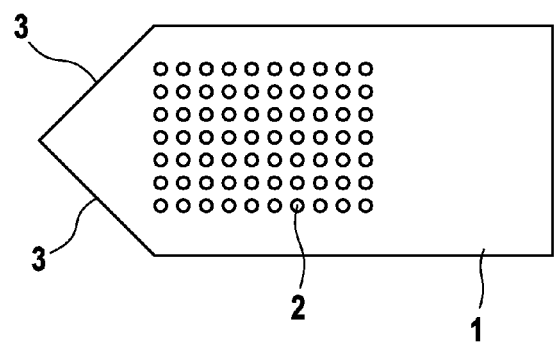
FIG. 1 shows a body fluid sampling device according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
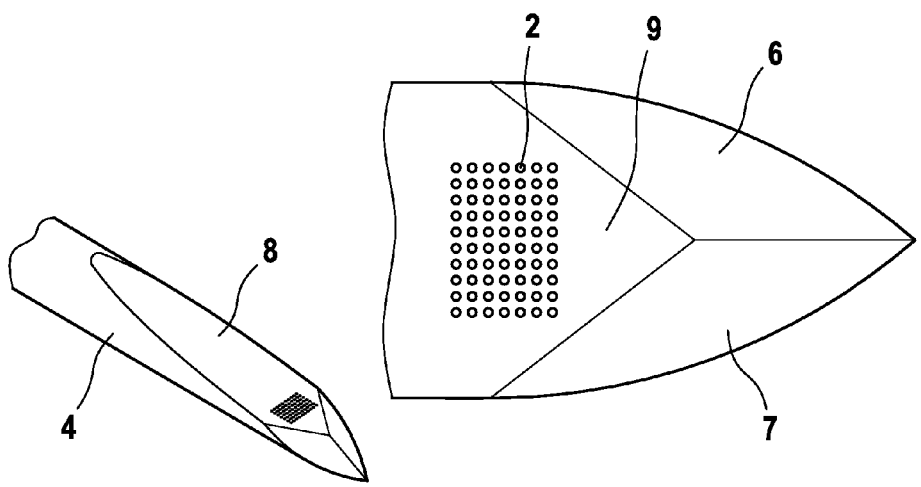
FIG. 2 shows a body fluid sampling device according to another embodiment.
Figure 3:
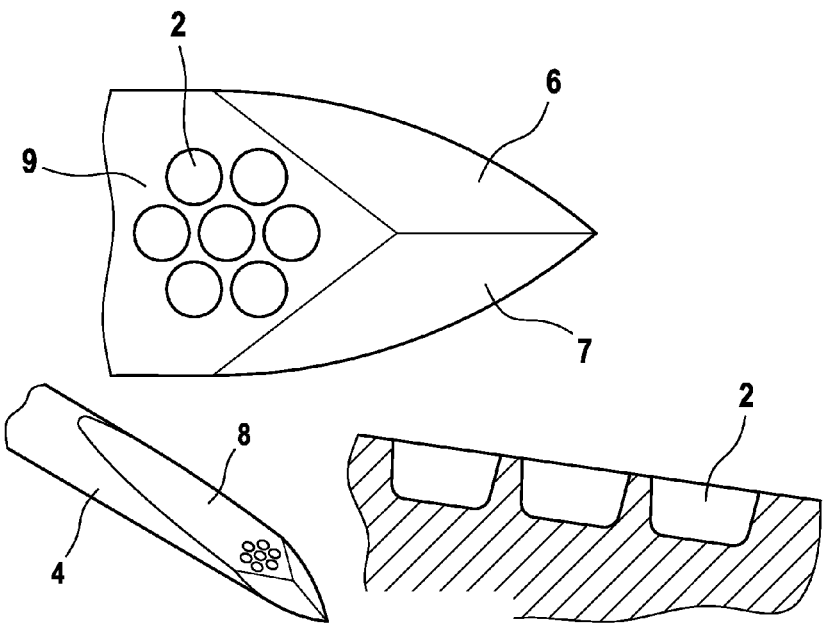
FIG. 3 shows a body fluid sampling device according to still yet another embodiment.
Figure 4:
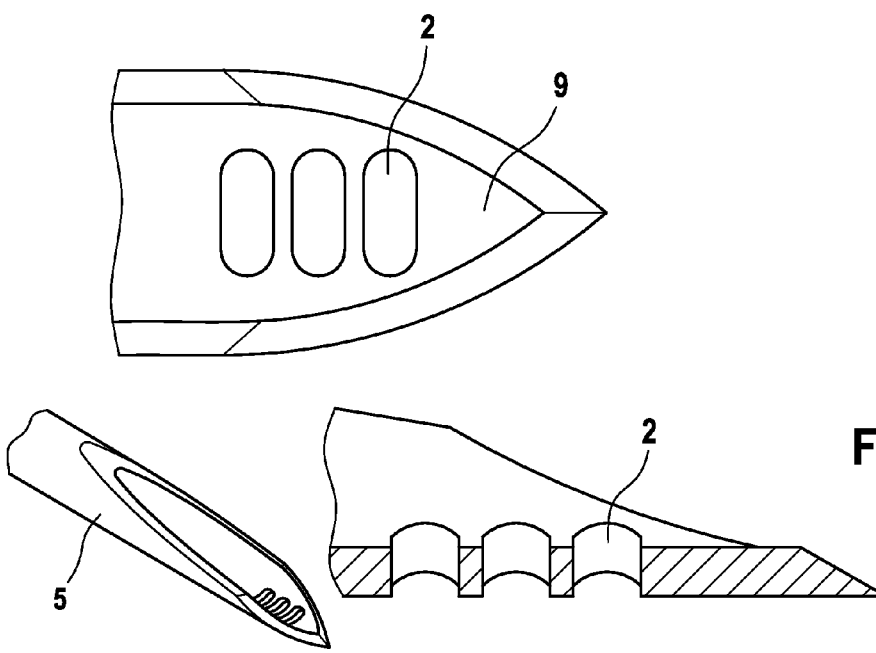
FIG. 4 shows an example of a hollow lancet comprising three elongated holes.

A preferred embodiment is described in FIG. 1. A body fluid sampling device according to one aspect the invention is shown, wherein the collection zone comprises holes or a porous surface in or on which the received body fluid is collected. It is preferred that the sampling device has 3 or more holes for receiving sample or even much more in case of porous surfaces. The depicted skin-piercing element is a flat lancet (1), e.g. made of stainless steel, silicon or a plastic carrier film with a thickness of 0.05 to 1 mm, preferably 0.2 mm, having small holes (2) near the piercing edges (3) of the lancet. The holes (2) may be through holes or blind holes, and may have a diameter of preferably 0.01 to 0.5 mm. The number of holes may vary from a few holes to a few hundred holes, preferred are 3 or more holes, even more preferred are 50 to 100 holes. A preferred diameter is around 20 µm. Alternatively the skin-piercing element may be a round solid (4) or hollow (5) lancet having sharpened surfaces with edges for piercing as shown in FIG. 2. Round lancets typically comprise three surfaces (6-8). Preferably a round, solid lancet may have the collection zone at its third surface (8). FIG. 2, for example, displays a collection zone (9) comprising 70 through holes (2) of 20 µm in diameter, FIG. 3 describes 7 blind holes (2) with a diameter of 0.15 mm and a depth of 80 µm. FIG. 4 shows an example of a hollow lancet (5) comprising three elongated through holes (2) in the range of 0.15 mm to 0.35 mm.

Further embodiments for a porous surface to collect the body fluid are roughened areas on one of the surfaces of the skin-piercing element, e.g. made by grinding. The grinding recesses form a repository to collect the body fluid. Alternatively pores may be applied to form the collection zone. These can be achieved e.g. by a porous coating or by selective etching of the lancet material, e.g. a special alloy of a resistant and a solvent metal, creating a spongy surface.

Especially when using flat lancets thin fibers of a second material may be incorporated into the surface, e.g. by rolling, that can be selectively etched.

According to the above embodiments it is possible that the direction of flow of fluid into the collection zone and out of it into a fluid receiving means is the same (e. g. in case of through holes the fluid receiving means is contacted with the side of the holes opposing the sample entrance) or the direction of flow may be reversed (fluid receiving means is contacted with the opening or holes into which sample is received).

As already stated above it is advantageous that the capillary channels are open to the outside such that they can take up body fluid while the capillary structure is inserted into the body.

The shape of the skin-piercing element is relatively uncritical. It can for example be in the form of a small cube. Special measures are usually not necessary to mount the skin-piercing element in a drive unit but a holding region located at the proximal end of the skin-piercing element is preferred. Advantageously the holding area is formed integral with the other regions of the skin-piercing element. Piercing element designs can be employed that are known for disposable lancets of conventional blood sampling systems. For example the holding region can have tapers into which spring elements of a holder of a drive unit engage in order to hold the piercing element. The piercing element is advantageously positioned within a holder in such a manner (for example by pressing the end of the piercing element facing away from the tip against a stop) that it allows a good control of the piercing depth. Reference is made to the document EP B 0 565 970 with regard to such a holder and the interaction between the holder and the disposable lancing unit.

A body fluid sampling device in addition to the skin-piercing element has a fluid receiving means which is spatially separated from the collection zone of the skin-piercing element in a way so that fluid in a fluid collection zone of the skin-piercing element will not contact the fluid receiving means during filling. The fluid receiving means and the collection zone, however, are contacted to each other after fluid sample has been received in at least a part of the collection zone and when start of the analytical reaction is desired. Such contacting primarily is a mechanical act where the channel holding the sample fluid and the fluid receiving means are moved together. This contacting includes pressing the fluid collection zone and fluid receiving means together or may mean a wiping movement.

Separation of skin-piercing element and fluid receiving means enables embodiments where the skin-piercing element is employed as a shuttle to transport sampled fluid to a fluid receiving means. This is particularly advantageous when fluid sampling is made in a spatially restricted area (e.g. the front end of apparatus) and the fluid receiving means does not fit well into this limited space. The latter in particular is the case for fluid receiving means fixed to a tape as, for example, described in EP 0 202 6242.4, U.S. Pat. No. 4,218,421 and EP 0 299 517. The shuttle function enables a testing process with the steps of pricking skin with the skin-piercing element
receiving body fluid in a collection zone of the skin-piercing element
contacting a portion of the collection zone with a fluid receiving means to provide a test zone with sample fluid
detecting a change of the test zone which relates to the concentration of an analyte.

In a preferred embodiment the transport means for transporting or shuttling and contacting the sampled body fluid with the fluid receiving means is done automatically. Preferred are but not restricting embodiments for automatic transfer are electrical, mechanical actuation, actuation by spring forces, manual actuation, e. g. by a user, pushing a slider, or a combination of these actuation principles. Particularly electrical motors may be employed to achieve the contacting.

The mentioned transport means can be controlled by a control unit which controls movement of the transport means including a spatial control as well as a timely control. By this the time for filling the sampling element, the timecourse of transportation, the time for contacting with a fluid receiving means and the time when the test zone is evaluated can be controlled. Such control improves fluid sampling and testing and therefore increases reliability.

Further a control unit in cooperation with a transport means can be employed to improve the sampling step. Particularly it is possible to withdraw the skin-piercing element only partially having it remaining in the skin but the lancing channel is already opened so that body fluid can emerge more easily and is taken up by the collection zone. It is even possible to rotate or move the skin-piercing element in the wound to improve the release of body fluid. For lancing skin with the skin-piercing element e. g. conventional spring type lancing units may be employed.

Further electrical drives for lancing as e. g. described in EP 1101443 may be employed. The mentioned electrical drives alone or combinations with other transport means may be employed for above described movements of the skin-piercing means.

In order to enhance sampling with the skin-piercing means vacuum may be employed to withdraw body fluid. Such vacuum can be applied to the skin area where skin-piercing is made or in case of a hollow sampling needle vacuum may be applied to the channel of the sampling needle.

The skin-piercing element may be transferred to the fluid receiving means to contact the skin-piercing element with the fluid receiving means by the above mentioned transport means. Additionally, the skin-piercing element may be transferred manually e. g. by the user, for example by using a lancet inserted in a skin-piercing device to pierce the skin and collect the body fluid sample. It may then be moved to a measurement instrument having a fluid receiving means inserted, and the collection zone is brought into contact to the fluid receiving means transferring the body fluid sample.

Test zones are especially prone to deterioration by humidity. Therefore test zones need to be sheltered in some way when stored. The skin-piercing means of the present invention can be employed to pierce a sealing of a sealed fluid receiving element. This is advantageous since additional means or steps for unpacking or opening of a sealing can be avoided.

According to the invention it is possible that the skin-piercing element is moved to the fluid receiving means, or that the fluid receiving means is moved to the skin-piercing element, or that both elements are moved.

When a magazine with fluid receiving means is employed there further can be the steps of 5 exposing a specific fluid receiving means from the stored fluid receiving means to contact the skin-piercing element loaded with sample fluid. When the specific fluid receiving means has been evaluated another fluid receiving means may be exposed to contact sample fluid on a skin-piercing element. It is possible that the used fluid receiving means is stored in the same magazine or in an additional waste magazine, or that the fluid receiving means is directly disposed, e. g. manually.

An automated system according to above shuttle concept therefore has one or more skin-piercing elements, a drive for driving a skin-piercing element to pierce skin, and a transport means to bring the skin-piercing element into contact with a fluid receiving means. The drive for piercing and the transport means may be employed in the same drive unit. Transport means can comprise for example electrical actuation, spring force actuation, manual actuation, e. g. by pushing a slider and a combination of these means. In a manual system according to above shuttle concept skin-piercing element and the fluid receiving means are in separated units and the transport to contact each other may be done manually, e. g. the user pricks the skin and collects the sample fluid with the skin-piercing element and then moves the skin-piercing element to the fluid receiving means, or vice versa, to contact the fluid sample with the fluid receiving means.

Although it is preferable to move the skin-piercing element to the fluid receiving means, it is also possible to transfer the fluid receiving means to the skin-piercing element, or to move both elements. Further the systems may comprise a storage unit for multiple fluid receiving means. The systems further may comprise an exposing unit for successively exposing fluid receiving means to receive fluid. The skin-piercing element may contact the fluid receiving means and the fluid sample is transferred on the fluid receiving means to the test zone, or the skin-piercing element may contact the test zone and the fluid sample is directly transferred to the test zone.

Further a fluid receiving means may be employed that has no test zone but a separate test zone is contacted with the fluid receiving means so that finally the test zone is wetted with sample fluid.

Figure 5:
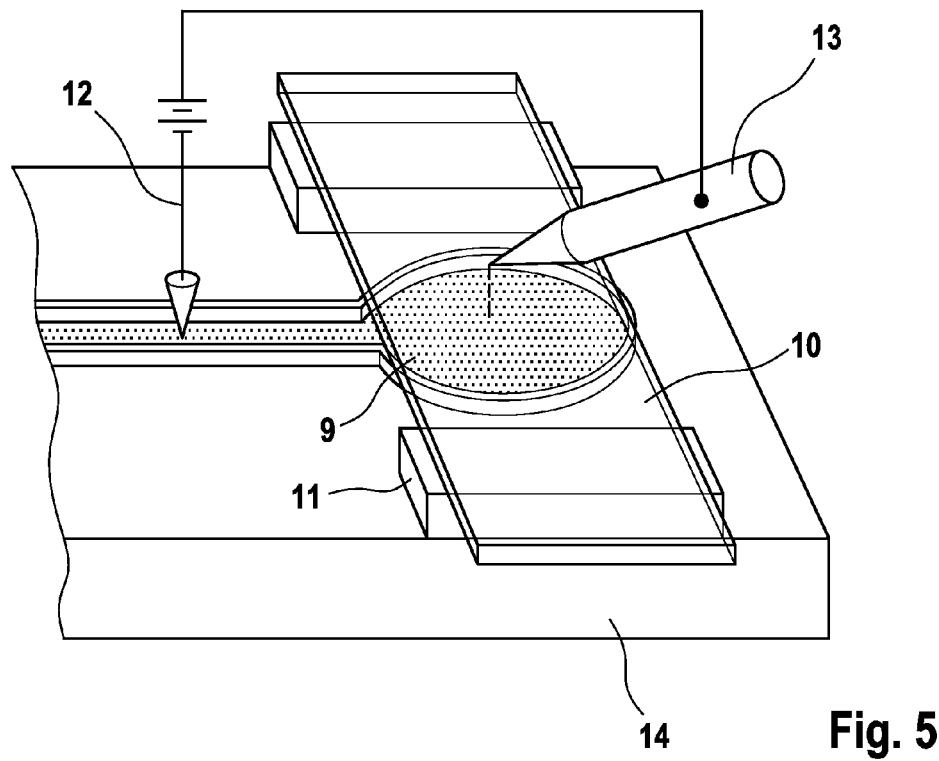
FIG. 5 shows the concept of electrical triggering a contact of sample fluid with a test zone.

The fluid receiving means is a structure that can take up fluid from a collection zone of the skin-piercing element. This uptake of fluid e.g. can be accomplished for example by an electrical potential applied between fluid in the collection zone and the fluid receiving means. FIG. 5 shows the concept of electrical triggering a contact of sample fluid with the test zone. A skin-piercing element (14) having a collection zone (9) is spaced from a fluid receiving means (10) by spacers (11). A high electrical potential is applied between an electrode (12) being in contact with the body fluid sample in the collection zone (9) and second electrode (13) contacted to the fluid receiving means. This may cause either fluid sample to move from the collection zone onto the test zone or may cause a movement of the fluid receiving means in direction of the collection zone. In both cases wetting of the test zone by sample fluid can be triggered in a very short time frame by turning on the electrical potential.

Preferably, the fluid receiving means has a higher capillarity than the collection zone of the skin-piercing element so that during contact fluid is automatically taken up, i. e. the capillarity difference serves as contacting means. In this regard the fluid receiving means can be made from a fleece or fabric material that has a high capillarity and is hydrophilic (at least in areas for fluid take-up). The fluid receiving means may have a particular region which comprises such material of high capillarity or the whole area of the fluid receiving means can act as receiving means for fluid from the fluid channel. The fluid receiving means may be a test zone in itself which can be covered with a fabric or woven material or the fluid receiving means may be more complex and allows for pre-processing of sample fluid and/or transport of fluid to a sensor/test zone. Pre-processing may comprise filtration of fluid sample and/or a mixing with reagents. Alternatively or to support the capillary force as contacting means a mechanical force can be applied pressing collection zone and receiving element together, or overpressure on the side of the collection zone and/or under pressure, e. g. vacuum, on the receiving side may be applied. In particular at collection zones comprising through holes overpressure on one end of the holes may be used to ensure that at least a portion of the sample leaves the collection zone through the other end and contacts the fluid receiving means. Mechanical compressing means or ultrasound, (e. g. in sawtooth operation), are also possible contacting means to transfer the fluid sample to the receiving means.

The fluid receiving means comprises a test zone with at least one chemistry layer that contains a reagent for detecting an analyte. The reagent undergoes a detectable change due to reaction with the analyte to be detected. Typical reagents for detecting glucose are based for example on glucose oxidase in conjunction with a chromogenic redox system. Reagents are well known in the prior art for optical evaluation which form a colour with glucose from the body fluid. Furthermore reagents are also known from the field of blood sugar test strips which allow electrochemical detection of analytes. The reagent mixtures that are used are usually in a solid state and, due to their constituents (e.g. aluminium oxide, kieselguhr and such like), have such a high capillarity that they can take up body fluid from the capillary channel. Since these detection systems are well-known from the prior art they are not described in more detail herein but reference is made to U.S. Pat. Nos. 5,762,770 and 36,268.

A preferred embodiment of a body fluid collection system according to the present invention additionally has a drive unit which, when activated, moves the skin-piercing element from a first into a second position such that it performs a lancing movement. Suitable drive units are well-known from the field of blood sampling systems. It can for example contain a spring which is cocked by the user and when released drives the skin-piercing element. A particularly advantageous drive unit is described in EP B 0 565 970.

Systems for body fluids analysis comprise a detection unit. If a sensor/test zone containing reagent is used which changes colour or forms a colour when an analyte is present, the system can have an optical detection unit comprising a light source and a detector to detect transmitted or reflected light. When electrochemical detection is employed, the system has electrodes which contact the test zone or the fluid receiving means. For evaluation of raw signals the system can have electronic devices known in the prior art in order to determine the concentration of analyte for example by measuring the so-called Cotrell current (see e. g. U.S. Pat. No. 36,268).

With the skin-piercing element according to the present invention body fluid can be withdrawn while the protruding portion is inserted in the skin or the protruding portion can be retracted from the body after piercing and takes up body fluid that emerges on the body surface. The producing portion comprising the collection zone in the body during the collection of the body fluid is preferred. A partial withdrawal in which the protruding portion remains in the body to collect body fluid is especially suitable for sampling at the arm. This is due to the fact that small incisions on the arm close very rapidly such that no fluid or only very small amounts of fluid emerge after piercing. On the other hand the sensitivity to pain is much less pronounced on the arm as compared for example to the finger and thus when the protruding portion remains in the body this is not felt to be painful.

Furthermore a withdrawal process can be carried out with the sampling device according to the invention which is a combination of the previously mentioned processes. In this combined process piercing is carried out firstly, the protruding portion may be pulled back over a part of the piercing path and to allowed to reside there for a collection period. Depending on the circumstances it may be possible to remove residual blood almost completely so that no blood is seen by the user.

A further decisive factor which is important for an efficient uptake of body fluid is the wettability of the collection zone. When capillary structures made of silicon are used, these are usually adequately wettable due to a silicon oxide layer on the surface. If metals are used for the capillary structure, these are often relatively difficult to wet. This can be counteracted by a number of different hydrophilisation measures such as silication of the surface. The wettability is usually adequate when the liquid in the capillaries has a concave meniscus which is the case when the wetting angle is less than 90°.

In a preferred embodiment of a body fluid collection system the volume of the fluid sample is very small, i. e. less than 0.5 µl, preferably 3 to 10 nl. Such a small volume can be collected very fast, e. g. using very small holes of for example 20 µm in diameter generating high capillary forces for rapid filling. The time to receive sufficient amount of body fluid sample can be less than 0,1 s, e. g. 1 to 10 ms Accordingly the interaction time between the skin-piercing element and the body while the skin-piercing element remains in the body and sufficient amount of body fluid sample is received may be less than 0.5 s, e. g. about 10 ms. Preferably the body fluid sample is collected in the body so that virtually no blood is visible on the skin. According to the invention the geometry of the collection zone and hence the body fluid volume that is collected is defined precisely, e. g. the risk of over- or underdosing of the fluid receiving means is significantly reduced.

Using a sampling device according to the invention the receiving of the body fluid sample may take less than 0.1 s, preferably 10 to 15 ms.

Figures 6A, 6B:
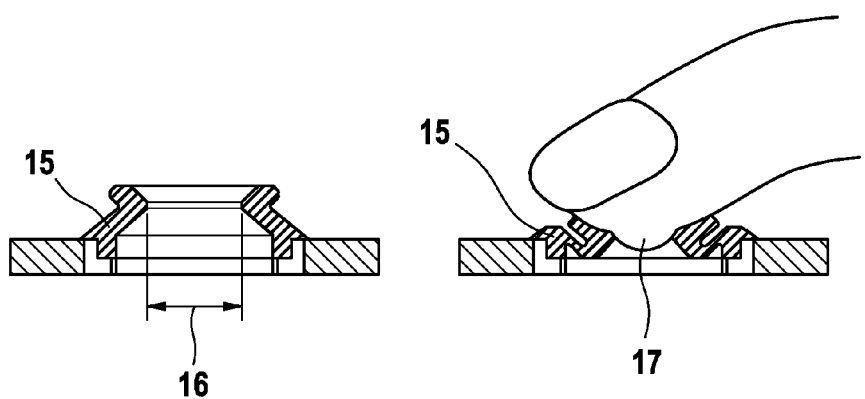
FIG. 6 shows a finger cone used to improve sample collection.

Advantageously an expression means to express sample fluid from a body portion may be employed in the present invention. An expression means may be a specially formed finger cone (15) to be used to improve sample collection as described in FIG. 6. It shows an example of the operation and action of a finger cone (15) according to U.S. Pat. No. 6,589, 260. As shown in FIGS. 6A and 6B a finger tip is pressed by the user onto the finger cone such that the finger cone is pressed together and the inner width (16) of the finger cone is reduced. As a result a part of the finger tip is squeezed and the internal pressure in this region (17) is increased. This design improves body fluid sampling in the collection zone and minimizes the body fluid leaking from the body. The inner width (16) should ideally be in the range of 8 to 11 mm in order to be suitable for large adult fingers as well as children's fingers.

A body fluid sampling system with an automatic transfer of the collection zone to the fluid receiving means according to the present invention is a fast one-step operation system which is easy to use even for elder, disabled or blind users. Due to the small sample volume that is collected the risk for contaminating the system components, especially the measurement instrument, is reduced promoting hygienic disposal of used fluid receiving means.

The high mass of the skin-piercing element compared to the very low fluid sample volume makes it easy to keep the temperature variation of the sample small, preferably below 10° C., e. g. by heating the skin-piercing element to a temperature of 20° C. to 40° C., preferably 30° C. For precise testing it is also preferred to provide a constant temperature in the testing region which is in the range between 20° C. to 40° C.

Advantageously skin-piercing elements and/or fluid receiving means may be provided in magazines. A possible embodiment may comprise, for example, a skin-piercing device with a magazine for skin-piercing elements and/or a fluid receiving means magazine as separated unit or e.g. integrated in the measurement instrument.

Figure 7:
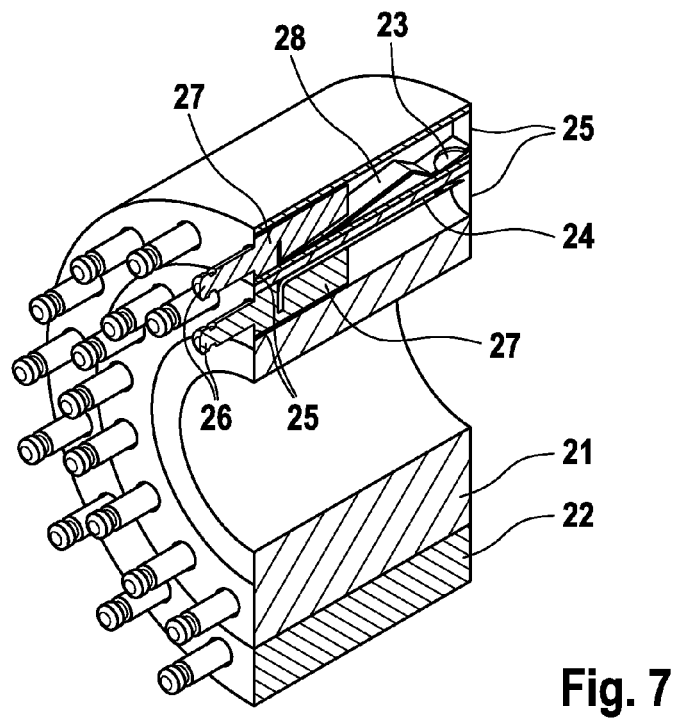
FIG. 7 shows an embodiment in which lancets and test strips are arranged in a drum magazine.
Figure 8:
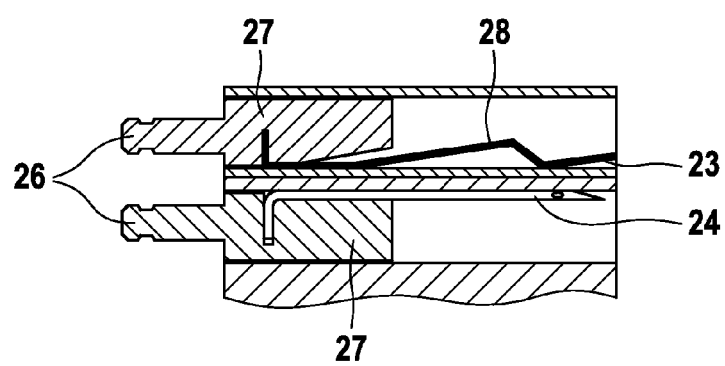
FIGS. 8, 9, 10, and 11 show various cross-sectional views of the FIG. 7 magazine during lancing and fluid collection.
Figure 9:
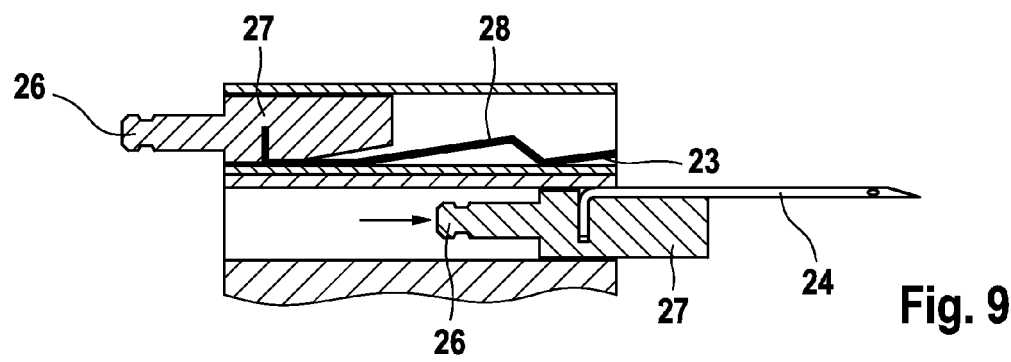
Figure 10:
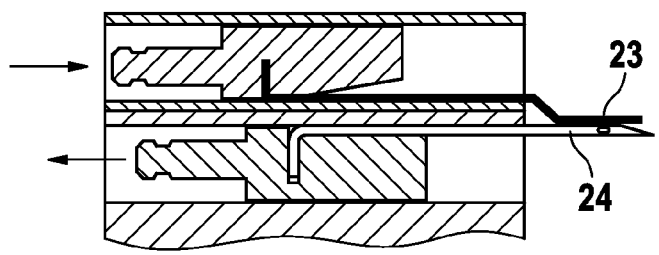
Figure 11:
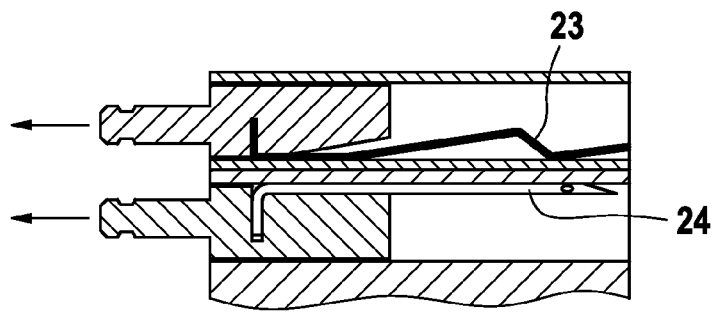

A preferred embodiment of lancets as skin-piercing elements and test strips as fluid receiving means arranged in a magazine according to the present invention is shown in FIGS. 7-11. FIGS. 7 and 8 describe a magazine (21) for skin piercing elements and a concentric outer test strip drum magazine (22) with separate chambers for each fluid receiving means (23). Each chamber is sealed by a foil and each element has an external grip to which a driving mechanism of the instrument can be connected to move the element out of the magazine and back into the magazine. Tearable foils (25) seal the chambers. The skin-piercing element and the fluid receiving means are each mounted on respective sliders (27) guiding the movement of the element. FIG. 9 shows a lancet (24) with a collecting zone being moved forward to penetrate skin and collect sample. During this movement the respective sealing foil is broken. FIG. 10 shows how the skin piercing element (24) is brought to a contacting position, e. g. by moving it back. The fluid receiving means (23) is also moved to the contacting position, e. g. by moving it forward. In a preferred embodiment the fluid receiving means is bend when stored in the cavity and comes to a position as shown in FIG. 10 when being moved out of it. By this the fluid receiving means comes into contact with the fluid collection zone. Alternatively fluid receiving means and skin-piercing element are pushing together by suitable actuation means. When the fluid receiving means is pressed against the collection zone of the element (24) the sample from the skin piercing element is transferred to the fluid receiving means to wet a test zone with sample. The test zone is for example read optically from the backside to confirm sample transfer and to determine glucose concentration. FIG. 11 shows how after the test is completed the used skin piercing element (24) and fluid receiving means (23) are drawn back into their respective drum chambers for storage.

In a fluid sampling system according to the invention preferably the collection direction of the body fluid sample flow entering the collection zone is not parallel, but preferably perpendicular, to the main actuation/lancing direction of the skin-piercing element.

A system according to the invention provides a disposable skin-piercing element and fluid receiving means avoiding direct contact of reagent chemistry and the body.

A skin piercing element may be made hydrophilic to improve the reception of body fluid. Hydrophilization may be conducted on the whole element or on selected regions.

In a preferred system according to the invention the body fluid sample collected in the collection zone is moved onto the fluid receiving means without using further body fluid as transfer means, i. e. the sample is transferred by mechanical, preferable electrical or manual means and not by fluid means. This method has the advantage that the body fluid can be transferred over a long distance if needed without increasing the dead volume, and the sample can be delivered to a small distinct spot, i. e. the test zone. Consequently the fluid receiving means size can be reduced.

Figure 12:
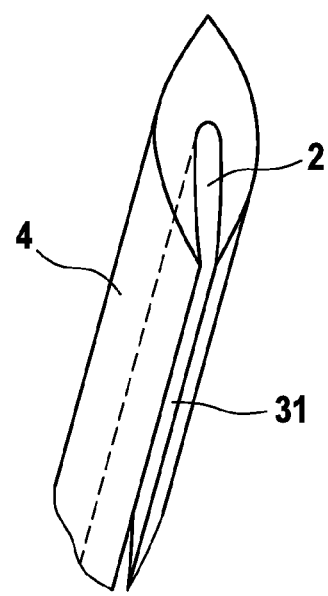
FIG. 12 shows a skin piercing element according to another embodiment that includes a round, solid lancet with a groove or recess to from a collection zone.

FIG. 12 shows another preferred embodiment of a skin-piercing element comprising a round, solid lancet (4) with a groove or recess (31), e. g. milled or etched, to form a collection zone (2).

Figure 13:
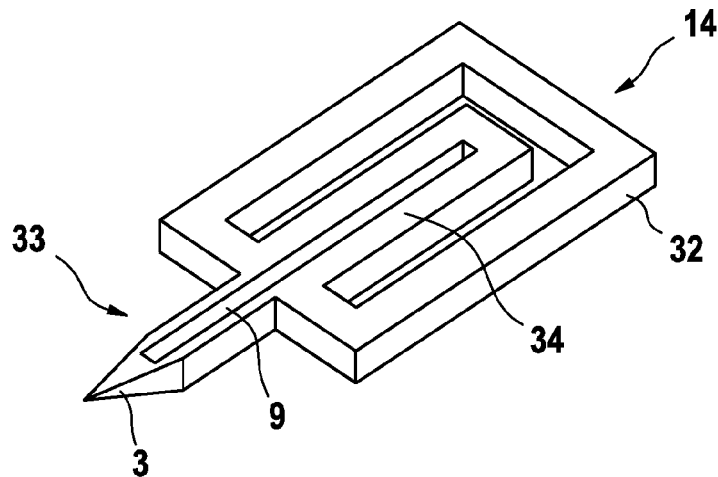
FIG. 13 shows a skin-piercing element according to still yet another embodiment.

FIG. 13 shows a skin-piercing element (14) which has a collection zone (9) which runs in an elongated portion of the skin-piercing element. This portion is connected to a holder (32) in form of a frame. The elongated portion has a protruding portion (33) which protrudes from the holder portion (32). At the front end of the protruding portion a sharpened tip (3) is located. The sharpened tip (3) enables penetration of the skin surface during pricking with the skin-piercing element. The collection zone (9) is located in the front end region of the protruding portion. The collection zone is an open capillary channel which permits body fluid which contacts the channel in the region of the protruding portion to move into the moveable portion of the collection zone (34) by means of capillary action. As depicted in FIG. 13 protruding portion (33), moveable portion (34) and frame portion (32) of the skin-piercing element (14) are formed integrally. The skin-piercing element (14) can be made by etching processes. As well known in silicon manufacturing processes a wafer of silicon material can be etched to provide devices comprising tips and capillary channels. For mass production it is however advantageous to produce the skin-piercing elements by etching of thin metal plates. It is particularly advantageous that the sharpened tip (3) of the protruding portion (33) can be formed during the etching process as well so as to avoid separate grinding steps. As can be seen from FIG. 13 there is no reagent or sensor contacting the fluid channel which would receive body fluid immediately after the collection zone has been filled with sample fluid. The present invention proposes to locate a test zone or sensor separately on a fluid receiving means.

Figure 14:
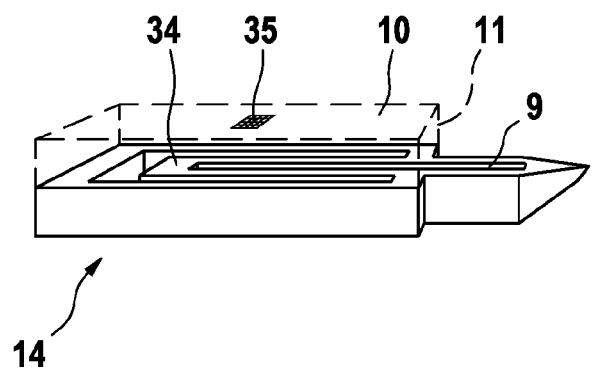
FIG. 14 shows the FIG. 13 skin-piercing element together with a fluid reciving means including a test zone.

FIG. 14 shows the skin-piercing element (14) of FIG. 13 together with a fluid receiving means (10) including a test zone (35). The fluid receiving means (10) is shown schematically. The fluid receiving means (10) is located on the upper side of the skin-piercing element (14) on which side the fluid channel (9) is open to the environment. The fluid receiving means (10) is, however, initially spaced from the collection zone (9) so that sample fluid within the collection zone does not contact the fluid receiving means. Therefore no fluid transfer from the collection zone onto the fluid receiving means occurs in this geometry of the fluid sampling device. In the depicted embodiment the fluid receiving means essentially consists of a holding structure (11) which provides proper orientation and spacing of the fluid receiving means relative to the skin-piercing element and the test zone (35). In the depicted embodiment the test zone includes a reagent which produces an optical signal based on the concentration of analyte in the body fluid. Due to the incorporation of porous materials as e.g. kieselghur or titanium dioxid, the reagent already has high capillarity that sucks fluid from capillary channel (9). The reagent is applied to a carrier surface. After fluid has been received in the collection zone and has filled the moveable section (34) the body fluid sampling device is primed for measurement. By means of mechanical actuation the moveable section (34) can be bend in direction of the sensor (35) so that body fluid located in the collection zone (9) contacts the test zone (35) and wettes the reagent. This mode of contacting the sensor with sample fluid has several advantages over the prior art devices.

A first advantage over the prior art is that measurement can be initiated at a specific point in time. This means that the time between wetting of the test zone and measurement of the final signal can be chosen at will. The time period, however, is shorter than the drying time of blood in the capillary. Knowing or controlling the time of reaction improves accuracy of the measurement. Further a signal can be measured beginning directly after wetting which allows to monitor reaction kinetics. Evaluation of this early signals can be used to improve accuracy of the measurement result as well.

Figure 15:
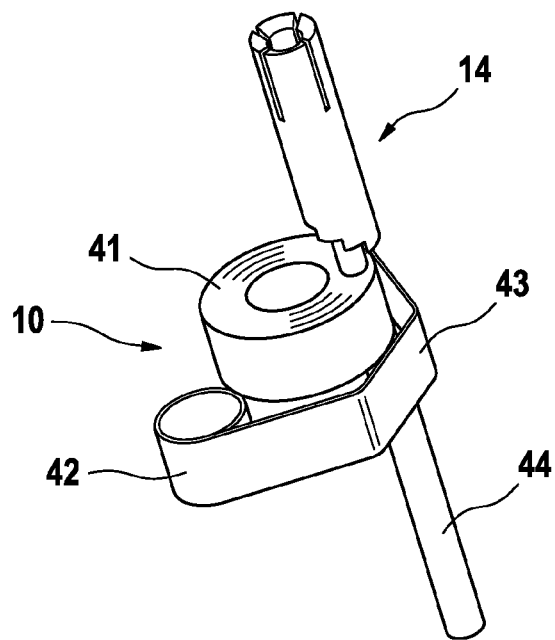
FIG. 15 shows a body fluid testing device that contains a plurality of test zones located on a test media cassette.

FIG. 15 describes a body fluid testing device that contains a plurality of test zones located on a test media cassette (10) serving as fluid receiving means which allows multiple testing (see e. g. EP 1 424 040). The cassette (10) includes a supply portion that stores an uncontaminated section (41) of the test media tape. A storage portion for storing a contaminated section (42) of the test media tape is further employed. The testing device is a handheld device that can be conveniently handled by a user. The test media tape (10) may be part of the testing device so that the whole device is discarded when the test media tape is used up or the test media tape may be arranged in a disposable cassette which is received in the testing device. The body fluid will be applied on a sensing region (43) which is positioned between the supply portion (41) and the storage portion (42) to sense an analyte of the body fluid collected on the test media cassette. The testing device further comprises a pricking unit (skin-piercing element, 14) for pricking a body portion. The pricking unit advantageously is arranged close to the sensing region.

Figure 16A:
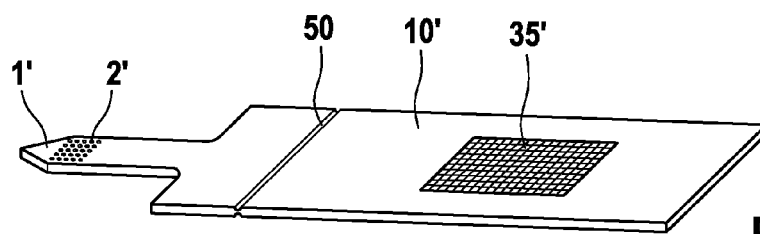
FIG. 16 shows an embodiment where a skin-piercing element that includes a collection zone and a fluid receiving means connected via a hinge.
Figure 16B:
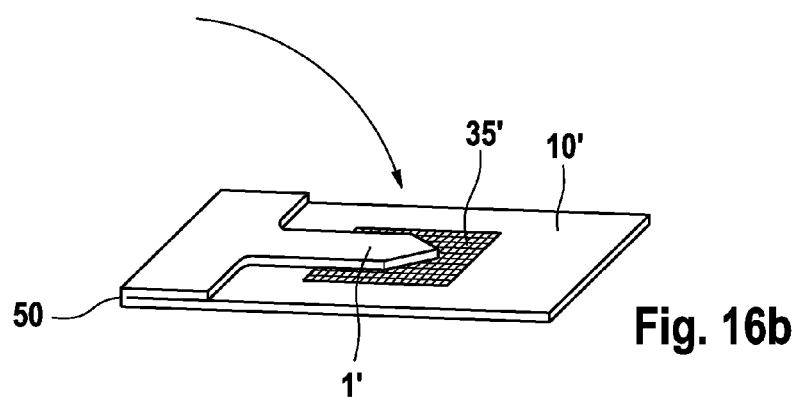
Figure 16C:
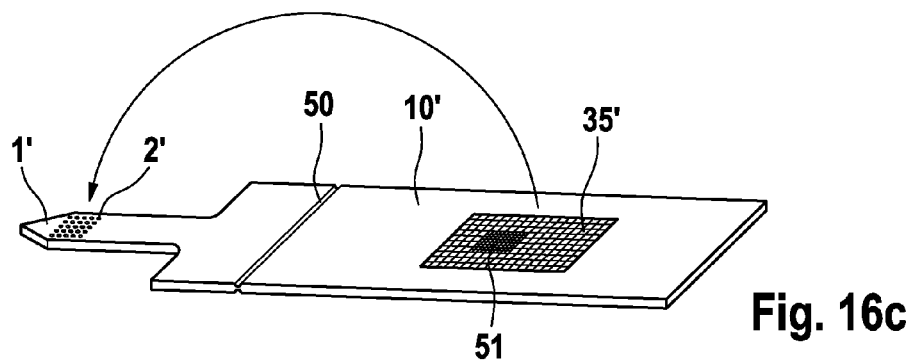

FIG. 16 shows an embodiment of the present invention where a skin piercing element (1') including a collection zone (2') and a fluid receiving means (10') are connected via a hinge (50). FIG. 16a) shows a configuration suitable for lancing skin and sampling body fluid with the collection zone (2'). The collection zone e. g. can be chosen according to the embodiments as described for FIG. 1 to 4. When fluid has been sampled the skin-piercing element is withdrawn and is folded so that the collection zone (2') contacts a test zone (35') on the receiving means. Measurement can be made in this folded configuration from beneath. However, it is also possible to unfold the device and to measure the colour of wetted portion (51) on the test zone (35') from the upper side as depicted in FIG. 16c).

Alternatively to folding an integrated sampling and testing device according to FIG. 16 it is also possible to rotate skin-piercing element and sample receiving means in a plane to contact sample on the skin piercing element with a test zone.

Figure 17A:
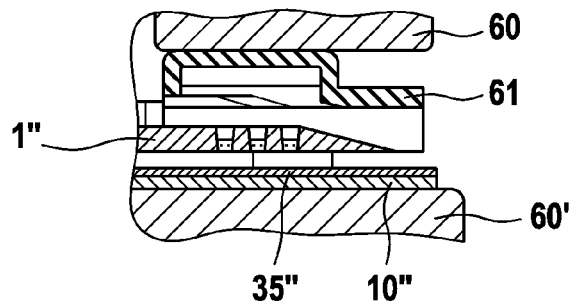
FIG. 17 shows a further embodiment to transfer a sample from a skin piercing element onto a test zone.
Figure 17B:
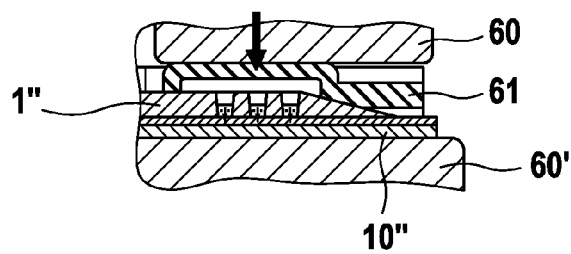
Figure 17C:
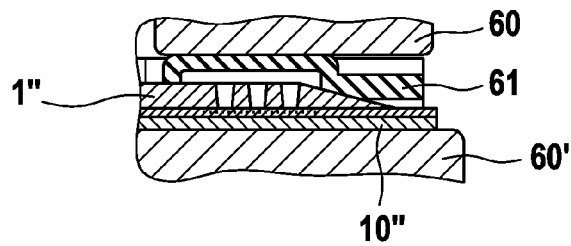

FIG. 17 depicts a further embodiment to transfer sample from a skin piercing element (1") onto a test zone (35"). FIG. 17a shows a skin piercing element that already has sampled fluid and has been retracted into a housing. Two parts (60, 60') are provided which press a rubber seal (61) onto the skin-piercing element so that a region which holds sampled fluid is sealed from one side. Application of further pressure squeezes the rubber seal and fluid from the skin piercing element is transferred onto test zone (35") lying underneath.

Instead or in addition to transfer fluid by contacting, fluid transfer is made via pneumatic actuation in this embodiment. Compared to devices according to e. g. WO 01/72220 where pneumatic actuation is employed too, here a relative movement of the skin-piercing element and the fluid receiving means (10") has been employed before the pneumatic actuation takes place. As described earlier on this allows to separate the lancing portion from the testing portion and hence sterilization can be made without destroying the test chemistry.

FIG. 17 further shows that sample fluid from holes in the collection zone of the skin-piercing element is transferred to opposing areas of the testing zone. The geometric pattern of the holes in the collection zone results in a similar pattern on the test zone. When conventional dry chemistries are employed the wetted areas on the test zone are initially roughly as large as the diameter of the holes in the collection zone and fluid moves vertically. It is preferred to evaluate the analyte dependent reaction from the side opposite to sample application to separate fluid transfer from the optics. Accordingly it is required to achieve complete wetting through the thickness of the test zone so that even the lowermost portion of the test zone reacts. Sufficient wetting e.g. is achieved if the thickness of the test zone is smaller than the depth of the holes in the collection zone. Preferably the thickness of the fluid receiving zone of the test zone is 10 to 80% of the depth of the holes in the collection zone. This means that very small thin skin-piercing elements can be employed as will become clearer by the following example. Today it is well feasible to produce dry chemistries having a liquid receiving structure with a thickness in the order of 10 to 50 micrometers only. To assure proper wetting the depth of the holes in the skin-piercing element only need to be in the order of 50 to 500 micrometers to collect sufficient fluid volumes even if the collecting holes are not completely filled. This in turn means that skin-piercing elements of this thickness or slightly more may be employed. Therefore it is preferred if the skin-piercing element has a thickness below 500, even more preferred below 250 micrometers. Skin-piercing means of the present invention therefore can be made roughly as thin as today's lancets which do not sample fluid. Although the sampled volume of collected fluid is in the nanoliter range only, reliable measurements can be achieved due to the availability of suitably thin dry chemistry test zones.

Figure 18A:
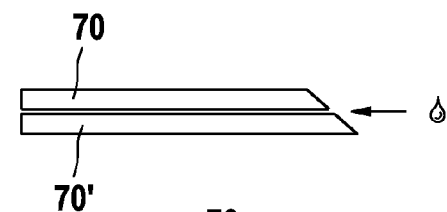
FIG. 18 shows a skin-piercing element having two parts which can be moved relative to one another.
Figure 18B:
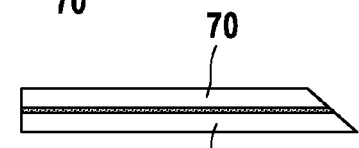
Figure 18C:
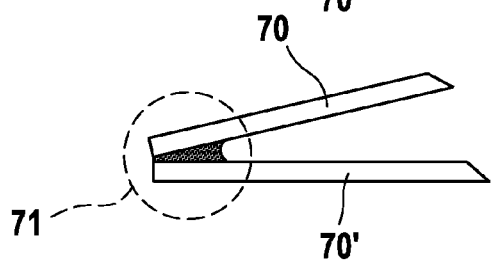

FIG. 18 shows a skin piercing element having two parts (70, 70') which can be moved relative to one another. In FIG. 18a the parts (70, 70') are aligned to form a capillary channel into which sample is received. The filled device (FIG. 18b) is rearranged as shown in FIG. 18c. At one end of the channel the parts are moved apart and hence the sample is concentrated in the region (71) where the parts are still close together.

Figure 19:
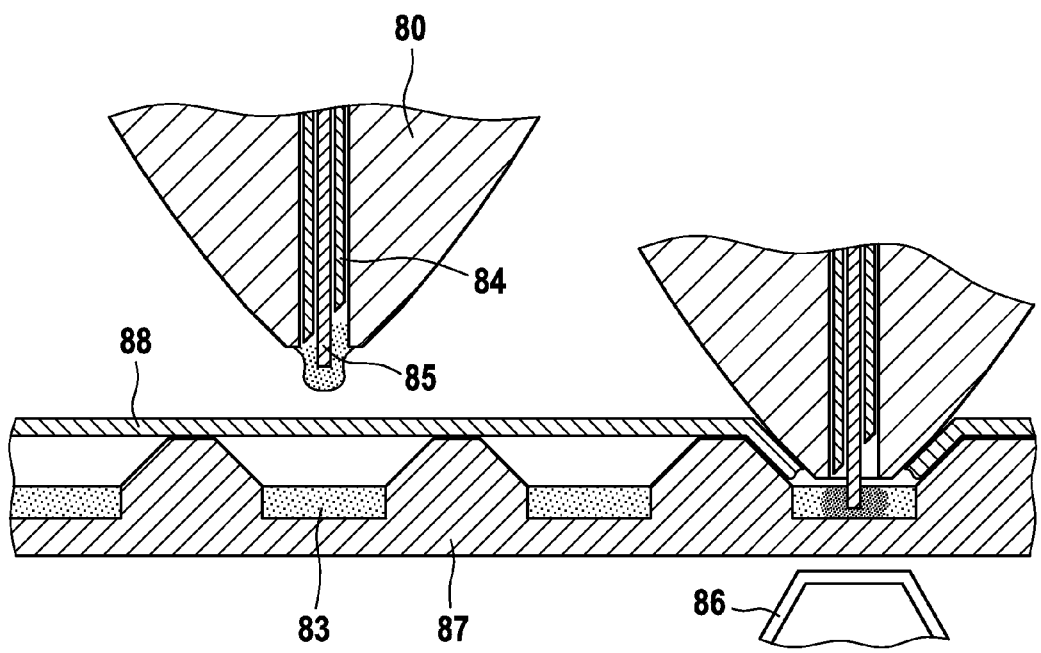
FIG. 19 shows an array of sealed fluid receving which are sealed against the environment by a sealing foil.

FIG. 19 shows an array of sealed fluid receiving means (83) which are sealed against the environment by a sealing foil (88) (e.g. an alumina laminate). The skin-piercing means (84) is located in a handheld device (80). The skin-piercing means as depicted is already filled with sample and is moved to the array of fluid receiving means. The skin-piercing element itself or as depicted a separate tip (85) may be employed to pierce the sealing foil. The tip of the skin-piercing element is then contacted with a test zone beneath the broken sealing foil to transfer sample fluid. Measurement of analyte concentration can be made from the underside with an optics (86) as shown schematically. To allow optical inspection the test zone is located on a transparent support (87).

Preferred features of the current invention are listed below:

Body fluid sampling device comprising a skin-piercing element having a collection zone for receiving body fluid and a fluid receiving means comprising a test zone and being spaced from said collection zone so that fluid in said collection zone will not contact the fluid receiving means, wherein said skin-piercing element has two or more collection zones.

Body fluid sampling device according to the invention, wherein the collection zone comprises through holes or blind holes.

Body fluid sampling device according to the invention, wherein the collection zone comprises through a rough surface or a recess to receive the body fluid.

Body fluid sampling device according to the invention, wherein the volume of the body fluid received by the sampling device is 3 to 10 nl.

Body fluid sampling device according to the invention, wherein the time of the skin-piercing element remaining in the body to receive the body fluid sample is 10 msec.

Body fluid sampling device according to the invention, wherein the time to receive a sufficient amount of the body fluid sample is less than 0.1 sec, preferably 1 to 10 msec.

System for body fluid analysis comprising a skin-piercing element with a collection zone for receiving body fluid, wherein at least a portion of said collection zone is open to the environment and a fluid receiving means remote from said collection zone so that fluid in said pathway will not contact the fluid receiving means, said fluid receiving means comprising a test zone, wherein said system comprises a meter with a detection unit for receiving signals from said test zone to determine the presence and/or concentration of analyte.

System according to the invention, wherein the meter includes a holder in which the fluid receiving means is received and signal transmission from the test zone to the detector is enabled.

System according to the invention, wherein said meter has a processing unit that receives a signal indicating that the contacting means has contacted the collection zone with the fluid receiving means or that sample fluid has reached the test zone.

System according to the invention, further comprising an exposing unit for successively exposing fluid receiving means from said magazine to receive fluid.

Method for determining an analyte concentration in body fluid comprising the steps of:
a) receiving body fluid in a collection zone of a skin-piercing element,
b) contacting the collection zone of the skin-piercing element with the fluid receiving means so that body fluid reaches a test zone on the fluid receiving means,
c) receiving signals from said test zone which are characteristic for an analyte concentration
d) processing said signals to determine the analyte concentration, wherein a time period beginning with step b) is monitored and determination of analyte concentration is initiated based on the time passed.

Method according to the invention, wherein step b) initiates a monitoring of signals and the change of signal over time is employed to determine a point in time for concentration determination.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

The invention claimed is:

1. Body fluid sampling device, comprising:
    a skin-piercing element having a sharpened end for piercing tissue and a collection zone for receiving body fluid from the tissue, the collection zone being exposed to the outside environment at the sharpened end of the skin-piercing element;
    a fluid receiving element connected to the skin-piercing element and comprising a test zone;
    the collection zone of the skin-piercing element being adapted to retain a sample of body fluid at the sharpened end and in isolation from the fluid receiving element when piercing the tissue; and
    the fluid receiving element being configured to contact the collection zone at the sharpened end of the skin-piercing element, when contacting the fluid receiving element, the collection zone transfers the body fluid directly to the fluid receiving element.

2. The device of claim 1, further comprising:
    the skin-piercing element and the fluid receiving element extending in a parallel manner with respect to one another; and
    the fluid receiving element being configured to contact the collection zone of the skin-piercing member in a perpendicular manner.

3. The device of claim 1, further comprising:
    the fluid receiving element being received in a chamber; and
    the fluid receiving element being stored in a bent state inside the chamber to contact the collection zone of the skin-piercing element when the fluid receiving element is extended from the chamber.

4. The device of claim 1, in which the fluid volume needed for measurement does not increase by increasing the distance between the collection zone and the fluid receiving element.

5. The device of claim 1, further comprising:
    a controller configured to move the skin-piercing element and the fluid receiving element from a non-contacting orientation to a contacting orientation;
    wherein at the non-contacting orientation the skin-piercing element and the fluid receiving element are spaced apart from one another; and
    wherein at the contacting orientation the skin-piercing element and the fluid receiving element are contacting one another.

6. The device of claim 1, in which the skin-piercing element is solid.

7. The device of claim 1, wherein the collection zone comprises holes in which the body fluid is collected.

8. The device of claim 7, wherein the holes are blind holes.

9. The device of claim 7, wherein the holes are through holes.

10. The device of claim 1, wherein the collection zone comprises a porous surface to receive the body fluid.

11. The device of claim 1, wherein the collection zone is a discrete structure configured to retain the discrete sample only at the sharpened end.

12. The device of claim 1, wherein the collection zone is adapted to retain at most 0.5 µl of body fluid.

13. The device of claim 1, wherein the device further comprises expression means.

14. The device of claim 13, wherein the expression means comprises a finger cone.

15. The device of claim 1, further comprising:
    a magazine in which the skin-piercing element and the fluid receiving element are arranged.

16. The device of claim 15, wherein the magazine includes a skin-piercing element drum in which the skin-piercing element is received and a test strip drum in which the fluid receiving element is received, the skin-piercing element drum and the test strip drum being arranged in a concentric manner.

17. The device of claim 16, wherein the test strip drum is received around the skin-piercing element drum.

18. The device of claim 16, wherein the skin-piercing element and the fluid receiving element are each mounted on respective sliders that have an external grip.

19. The device of claim 18, further comprising:
    the test strip drum defining a chamber in which the fluid receiving element is received; and
    the fluid receiving element being bent to contact the collection zone of the skin-piercing element when the fluid receiving element is extended from the chamber.

20. The device of claim 19, further comprising:
    a foil sealing the chamber.

21. The device of claim 1, wherein the fluid receiving element is bent to contact the collection zone of the skin-piercing element when the fluid receiving element is extended.

22. The device of claim 1, wherein skin-piercing element includes a solid lancet with a groove that forms the collection zone.

23. The device of claim 1, further comprising a cartridge connected to the skin-piercing element and connected to the fluid receiving element, wherein the skin-piercing element and the fluid receiving element are connected to one another through their individual connections to the cartridge.

24. Body fluid sampling device, comprising:
    a skin-piercing element having a sharpened end for piercing tissue and a collection zone for receiving body fluid from the tissue, the collection zone being exposed to the outside environment at the sharpened end of the skin-piercing element;
    a fluid receiving element connected to the skin-piercing element and comprising a test zone;
    the skin-piercing element lacking a fluid path for directly transporting the body fluid from the collection zone to the fluid receiving element when piercing the tissue, the collection zone being isolated at the sharpened end and configured to retain a sample of the body fluid at a discrete location at the sharpened end, the discrete location terminating before fluidically connecting with the fluid receiving element when the skin-piercing element is piercing the tissue;
    the skin-piercing element and the fluid receiving element extending in a parallel manner with respect to one another; and
    the fluid receiving element being configured to contact the collection zone of the skin-piercing member in a perpendicular manner.

25. The device of claim 24, further comprising:
    the fluid receiving element being received in a chamber; and
    the fluid receiving element being stored in a bent state inside the chamber to contact the collection zone of the skin-piercing element when the fluid receiving element is extended from the chamber.

26. The device of claim 24, in which the fluid volume needed for measurement does not increase by increasing the distance between the collection zone and the fluid receiving element.

27. The device of claim 24, further comprising:
a controller configured to move the skin-piercing element and the fluid receiving element from a non-contacting orientation to a contacting orientation;
wherein at the non-contacting orientation the skin-piercing element and the fluid receiving element are spaced apart from one another; and
wherein at the contacting orientation the skin-piercing element and the fluid receiving element are contacting one another.

28. The device of claim 24, in which the skin-piercing element is solid.

29. The device of claim 24, wherein the collection zone comprises holes in which the body fluid is collected.

30. The device of claim 29, wherein the holes are blind holes.

31. The device of claim 29, wherein the holes are through holes.

32. The device of claim 24, wherein the collection zone comprises a porous surface to receive the body fluid.

33. The device of claim 24, wherein the collection zone is a discrete structure configured to retain the discrete sample only at the sharpened end.

34. The device of claim 24, wherein the collection zone is adapted to retain at most 0.5 µl of body fluid.

35. The device of claim 24, wherein the device further comprises expression means.

36. The device of claim 35, wherein the expression means comprises a finger cone.

37. The device of claim 24, further comprising:
a magazine in which the skin-piercing element and the fluid receiving element are arranged.

38. The device of claim 37, wherein the magazine includes a skin-piercing element drum in which the skin-piercing element is received and a test strip drum in which the fluid receiving element is received, the skin-piercing element drum and the test strip drum being arranged in a concentric manner.

39. The device of claim 38, wherein the test strip drum is received around the skin-piercing element drum.

40. The device of claim 38, wherein the skin-piercing element and the fluid receiving element are each mounted on respective sliders that have an external grip.

41. The device of claim 40, further comprising:
the test strip drum defining a chamber in which the fluid receiving element is received; and
the fluid receiving element being bent to contact the collection zone of the skin-piercing element when the fluid receiving element is extended from the chamber.

42. The device of claim 41, further comprising:
a foil sealing the chamber.

43. The device of claim 24, wherein the fluid receiving element is bent to contact the collection zone of the skin-piercing element when the fluid receiving element is extended.

44. The device of claim 24, wherein skin-piercing element includes a solid lancet with a groove that forms the collection zone.

45. The device of claim 24, further comprising a cartridge connected to the skin-piercing element and connected to the fluid receiving element, wherein the skin-piercing element and the fluid receiving element are connected to one another through their individual connections to the cartridge.

* * * * *

UNITED STATES PATENT AND TRADEMARK OFFICE
CERTIFICATE OF CORRECTION

PATENT NO. : 7,819,822 B2  
APPLICATION NO. : 11/470368  
DATED : October 26, 2010  
INVENTOR(S) : Irio G. Calasso et al.

It is certified that error appears in the above-identified patent and that said Letters Patent is hereby corrected as shown below:

Title page 1, item 30 under the "Foreign Application Priority Data" section, change the EP publication number "04005385" to --04005385.2--.

Column 9, line 15, change "the steps of 5 exposing a specific fluid" to --the steps of exposing a specific fluid--.

Signed and Sealed this  
Eleventh Day of January, 2011

David J. Kappos  
*Director of the United States Patent and Trademark Office*